US007656526B1

(12) United States Patent
Spuler et al.

(10) Patent No.: US 7,656,526 B1
(45) Date of Patent: Feb. 2, 2010

(54) LIDAR SYSTEM FOR REMOTE DETERMINATION OF CALIBRATED, ABSOLUTE AEROSOL BACKSCATTER COEFFICIENTS

(75) Inventors: Scott Spuler, Westminster, CO (US); Shane Mayor, Boulder, CO (US)

(73) Assignee: University Corporation for Atmospheric Research, Boulder, CO (US)

( * ) Notice: Subject to any disclaimer, the term of this patent is extended or adjusted under 35 U.S.C. 154(b) by 189 days.

(21) Appl. No.: 11/459,269

(22) Filed: Jul. 21, 2006

(51) Int. Cl.
*G01N 15/02* (2006.01)
*G01N 21/00* (2006.01)

(52) U.S. Cl. ...................... 356/336; 356/342
(58) Field of Classification Search .......... 356/335–343
See application file for complete search history.

(56) References Cited

U.S. PATENT DOCUMENTS

| 3,554,105 | A | * | 1/1971 | Dougherty | 396/241 |
|---|---|---|---|---|---|
| 3,788,742 | A | * | 1/1974 | Garbuny | 356/5.03 |
| 4,059,356 | A | * | 11/1977 | Kebabian | 356/435 |
| 4,397,549 | A | * | 8/1983 | Morgan | 356/5.01 |
| 4,554,666 | A | * | 11/1985 | Altman | 372/19 |
| 4,854,705 | A | * | 8/1989 | Bachalo | 356/336 |
| 4,858,238 | A | * | 8/1989 | Cardimona | 372/3 |
| 5,241,315 | A | * | 8/1993 | Spinhirne | 342/54 |
| 5,373,367 | A | * | 12/1994 | DeGunther et al. | 356/438 |
| 5,451,787 | A | * | 9/1995 | Taylor | 250/338.5 |
| 6,404,494 | B1 | * | 6/2002 | Masonis et al. | 356/338 |
| 6,542,226 | B1 | * | 4/2003 | Wernet | 356/28.5 |
| 6,556,282 | B2 | * | 4/2003 | Jamieson et al. | 356/4.01 |
| 6,593,582 | B2 | * | 7/2003 | Lee et al. | 250/458.1 |
| 6,894,768 | B2 | * | 5/2005 | Caldwell et al. | 356/28 |
| 7,151,787 | B2 | * | 12/2006 | Kulp et al. | 372/70 |
| 2003/0197863 | A1 | * | 10/2003 | Snelling et al. | 356/337 |

* cited by examiner

*Primary Examiner*—Gregory J Toatley, Jr.
*Assistant Examiner*—Jarreas C Underwood
(74) *Attorney, Agent, or Firm*—Marsh Fischmann & Breyfogle LLP (57) ABSTRACT

A lidar system capable of remotely identifying calibrated absolute aerosol backscatter coefficients of atmospheric aerosol particles by transmitting a beam of light and spectrally separating the intensity of Rayleigh and Mie backscattering is disclosed. The transmitter features high pulse energy to generate sufficient Rayleigh backscattering, enabling atmospheric scanning in a timely manner. The transmitter employs a seeded Nd:YAG laser and a seeded stimulated Raman scattering wavelength shifter to achieve narrow bandwidth, eye-safe laser pulses. The receiver employs a telescope, collimating lens, beam splitter, molecular absorption filter, focusing lenses, and avalanche photodiodes. Mie backscattering is blocked by the molecular absorption filter to provide a Rayleigh signal, which is used with knowledge of atmospheric density to calibrate the Mie signal. The system is intended for atmospheric research and aerosol monitoring applications where calibrated Mie scattering intensity is necessary to measure the optical depths of aerosol structures such as plumes, clouds, and layers.

2 Claims, 7 Drawing Sheets

LIDAR SYSTEM FOR REMOTE DETERMINATION OF CALIBRATED, ABSOLUTE AEROSOL BACKSCATTER COEFFICIENTS

GOVERNMENT SUPPORT

The present invention was made with Government support under Cooperative Agreement No. ATM-0301213 awarded by the National Science Foundation. The Government has certain rights in this invention.

FIELD OF THE INVENTION

This invention relates to laser radars or lidars in general and more particularly to a lidar system suitable for defense, scientific, environmental and commercial applications requiring long range remote identification of a calibrated, absolute aerosol backscatter coefficient for a section of atmosphere.

BACKGROUND OF THE INVENTION

It is often desirable to know absolute values for optical properties of atmospheric aerosol particles. For example, it may be beneficial to know the absolute aerosol backscatter coefficient of aerosol particles in a section of interest in the atmosphere. The value of an absolute aerosol backscatter coefficient represents the ability of atmospheric aerosol particles in a particular section of atmosphere to scatter optical energy propagating through that particular section of atmosphere. Since an absolute aerosol backscatter coefficient is obtained by calibrating the lidar system with respect to molecular scattering and applying that calibration factor to the aerosol backscatter detected, the resulting value for the absolute aerosol backscatter coefficient is calibrated. Therefore, absolute aerosol backscatter coefficient measurements, as opposed to measurements of uncalibrated, relative aerosol backscatter intensity, allow for direct comparison of measured absolute aerosol backscatter coefficient values from differing locations and dates. The absolute aerosol backscatter coefficient data can also be expressed with units, such as per meter per steradian.

The remote identification of absolute aerosol backscatter coefficients for significant sections of the atmosphere is critical in many applications. One such area is the remote measurement of biological, chemical or radiological agents in the atmosphere. The potential of intentional releases of biological, chemical or radiological contaminants into the atmosphere is a real and serious threat to civilian populations in the United States and abroad and also to military personnel throughout the world. It would be beneficial to be able to determine and monitor the absolute aerosol backscatter coefficient of a plume of suspected or known harmful aerosol particles. This information could be used to help identify particle concentration and diffusion characteristics. This would be valuable information in standoff detection and homeland security situations where the information could be used to predict the lethality of a pathogenic aerosol cloud.

Absolute aerosol backscatter coefficients can be used to determine the optical thickness of aerosol particles in a section of atmosphere. Also, particle concentration can be obtained when measuring a plume consisting of particles of an identified type if the size distribution and scattering efficiency of that type of aerosol particle is known. This data can be valuable to atmospheric researchers and modelers attempting to determine the climatic effects of atmospheric particles. For example, scientists attempting to determine the effects of pollution on global warming would find real-world absolute aerosol backscatter coefficient data valuable in modeling current and future effects of pollution. The data could also be coupled to corresponding climate conditions present when the measurements were taken. Scientists would also find valuable the ability to monitor the effects and particle distribution of large-scale natural events such as dust storms, forest fires and volcanic eruptions by determining absolute aerosol particle backscattering coefficients in various locations after such events.

High Spectral Resolution Lidar (HSRL) is a known technique in the lidar community for determining absolute aerosol backscatter coefficients. However, a number of factors limit the performance of known HSRL systems. One such limitation is that known HSRL systems operate at relatively short wavelengths. These short wavelengths correspond to wavelengths where the human eye is particularly vulnerable to injury. Therefore, extreme care must be taken when operating an HSRL system at such a wavelength.

Generally, there are two ways in which current HSRL systems operate. First, some current systems transmit relatively weak pulses to operate in an eye-safe manner. The relatively weak pulses in turn require these systems to time average backscatter readings over a relatively long period of time resulting in low temporal resolution and the lack of ability to scan significant sections of the atmosphere rapidly. This lack of ability to scan rapidly limits the ability of these types of HSRL systems to track large atmospheric structures, such as plumes of aerosol particles.

Second, some current systems transmit higher pulse energies at the aforementioned relatively short wavelengths and do not operate in an eye-safe manner. Operation in this manner requires extraordinary safety precautions, such as verifying that the intended path of the transmitted beam is clear of any humans, such as pilots in passing planes, who could be harmed by the beam. This severely limits the use of these systems and prevents these systems from operating in a continuous, unattended fashion.

SUMMARY OF THE INVENTION

The present invention relates to a lidar system, lidar system components, and associated methodologies for remote measurement of absolute aerosol backscatter coefficients. In particular, one embodiment includes a transmitter that enables transmission of an eye-safe, high pulse energy, narrow bandwidth, and optical beam. A receiver and processor capable of distinguishing molecular scattered (e.g., Rayleigh scattered) radiation from aerosol scattered (e.g., Mie scattered) radiation is provided, enabling the determination of absolute aerosol backscatter coefficients. This is accomplished by filtering out the aerosol scattering component of the detected backscattered radiation. The aerosol-scattered component is extremely spectrally narrow and corresponds to the aforementioned narrow bandwidth transmission wavelength. The remaining scatter detected is substantially the molecular scattering component of the backscatter. At a known temperature and pressure, the molecular backscatter coefficient can be predicted. The aerosol scattering component can be measured by subtracting the molecular scattering component from the total backscatter measured. The remainder will substantially be the aerosol scattering component of the backscatter. From the measured molecular and aerosol scattering components and the molecular backscatter coefficient, a calibrated, absolute aerosol backscatter coefficient can be calculated.

The absolute aerosol backscatter coefficient determined by an embodiment of the present invention can be used to identify the optical thickness of aerosol particles in the atmosphere. When the type of aerosol particle causing the scattering is unknown the optical thickness of the particles is of value in that it can be used to predict the effects of the aerosol particles on light passing through the aerosol particle aggregate structure or layer. This is critical when studying or predicting the effects of aerosol particles on weather and climate. In particular it is useful to researchers studying global warming who are interested in the optical thickness of atmospheric aerosol particles to help, for example, model the effects of those particles on sunlight entering the atmosphere.

An embodiment of the present invention is capable of helping to determine particle concentration when certain characteristics, such as size distribution and scattering efficiency, of the type of aerosol particle present in the atmosphere are known. Knowing particle concentration can be valuable when, for example, determining the amount of pollution being emitted from an industrial facility or determining the amount of ash or dust from a natural disaster. Concentration level information can be particularly critical when the atmospheric aerosol particles are harmful, intentionally released biological, radiological or chemical agents. Concentration levels, plume location and plume movement would be valuable to emergency responders to help determine evacuation areas and routes, predict health effects on the endangered population and direct emergency response efforts.

The present inventors have recognized that there exists a need for a remote absolute aerosol particle backscatter coefficient identification system that can safely, quickly and efficiently identify the aerosol scattering component of backscattered radiation without the need for extraordinary safety precautions or lengthy time-averaging of backscattered radiation to achieve acceptable signal-to-noise ratios. The present inventors have also recognized the need for a remote absolute aerosol particle backscatter coefficient identification system that can scan the atmosphere at a rate sufficient enough to provide accurate and timely information about the structure and movement of the aerosol particles.

Accordingly, one embodiment of the present invention is capable of rapidly determining a calibrated, absolute aerosol backscatter coefficient from the backscattered radiation of a transmitted pulsed beam. The backscattered radiation may be integrated over a very short period of time, e.g. a single or small number of pulses. One implementation is capable of determining a calibrated, absolute aerosol backscatter coefficient of aerosol plumes from a single laser pulse to ranges of several kilometers. This is possible because of the high pulse energy which generates sufficient backscatter signal that can be distributed across at least two detectors (e.g., unfiltered or combined channel and filtered or molecular channel) from a single pulse. Because of the high pulse energy, analog direct detection can be used in the system as opposed to photon counting receivers used in known, relatively low pulse energy HSRL systems. This enables the embodiment to scan significant sections of the atmosphere in a timely manner. This further enables the present embodiment to provide data that can be used to generate a dynamic representation of the absolute aerosol backscattering attributes of aerosol particles in large sections of the atmosphere. Also it is beneficial that the system is capable of operating in an eye-safe mode in that it produces an energy output within the eye-safety standards of American National Standard for the Safe Use of Lasers, ANSI Z136.1-2000, which is incorporated herein by reference.

Preferably, as stated above, an embodiment of the present invention should produce sufficient backscatter energy to support the aerosol particle characterization within a reasonably short time window. Accordingly, achieving high temporal identification of the aerosol scattering component of backscattered radiation involves a number of parameters and issues at the component and system levels. Identifying and addressing these issues provides a significant motivation related to the various aspects of the invention as set forth below.

Furthermore, the present inventors have recognized that it would be useful to remotely parameterize aerosol particles in multiple ways. Accordingly, embodiments of the present invention may be integrated into a system of remote aerosol particle identification and tracking. Other parameters, such as, for example, fluorescence and depolarization characteristics, may, in combination with the aerosol scattering information, aid in identifying unknown aerosol particles. This remote parameterization can be accomplished by the analysis of returned radiation from transmitted radiation that interacts with atmospheric aerosol particles to determine aerosol particle parameters such as, for example, particle density, optical thickness, particle shape, particle behavior and chemical composition. The analysis can be comprised of examining such characteristics as molecular and aerosol scattering (as presented herein), depolarization, fluorescence, wave properties, and other optical phenomenon. The analysis of the molecular and aerosol scattering attributes of backscattered radiation to remotely determine aerosol particle characteristics described herein is a promising aspect of the broader ability to remotely characterize atmospheric aerosol particles using a transmitted beam of radiation.

In accordance with one aspect of the present invention, a lidar system capable of remote identification of a molecular scattering component of backscattered radiation is provided where the transmitter is capable of transmitting an optical beam having a primary wavelength between about 1.5 and 1.8 microns. The system also comprises a receiver capable of detecting the backscatter from the transmitted beam and converting the detected backscatter into electrical signals that form an electrical signature. The electrical signature may include information representing the molecular scattered component of backscattered radiation. The system may further comprise a processor capable of determining the molecular scattered component of the detected backscattered radiation. The lidar system may also be capable of determining an aerosol-scattered component of the backscattered radiation. The lidar system may also be capable of determining a calibrated, absolute aerosol backscatter coefficient based on, at least in part, analysis of the received backscatter. The lidar system may also be capable of determining the optical thickness of atmospheric aerosol particles based on the analysis of the electrical signals generated by the detected backscatter to radiation.

Furthermore, the optical beam transmitted by the lidar system may have an energy level within the eye safety standards of American National Standard for the Safe Use of Lasers, ANSI Z136.1-2000. The transmitted optical beam may have a wavelength of 1.543 microns. The optical beam may have a linewidth equal to or smaller than a single absorption line of hydrogen cyanide ($H^{13}C^{14}N$). Specifically, in one embodiment, the second line of the P branch of hydrogen cyanide is used.

The transmitter of the lidar system may be comprised of a source laser pump for providing a source beam and a Raman wavelength shifter for shifting the wavelength of the source beam to a second wavelength between about the 1.5 and 1.8 microns. For example, the source laser pump may be an Nd:YAG laser pump generally producing a 1064 nm wavelength beam. The source laser pump may be seeded by a source laser seed laser, which may be a fiber injection seed laser. The source laser seed laser may be tunable to allow for the fine adjustment of the wavelength of the source beam. The Raman wavelength shifter may be seeded by a Raman wavelength shifter seed laser. The Raman wavelength shifter seed laser may be tunable to allow for the fine adjustment of the wavelength of the Raman shifted beam. The source beam may be amplified prior to entering the Raman wavelength shifter. The transmitter of the lidar system may transmit an optical beam having a bandwidth of less than about 200 MHz. The transmitted optical beam may have a pulse energy of at least about 200 mJ/pulse.

The receiver of the lidar system may be comprised of collection optics for collecting backscattered radiation, a collimator for collimating the collected backscattered radiation, a beam splitter for splitting the collimated backscattered radiation into a first post-beam-splitter beam and the second post-beam-splitter beam, first directing optics for directing the first post-beam-splitter beam onto a first detector, and second directing optics for directing the second post-beam-splitter beam into a wavelength filter and onto a second detector. Both the first and second detectors may be operative for converting the beam received by each detector into electrical signals representative of their respective received beams. The first detector may be a combined channel detector and the second detector may be a molecular channel detector.

Still referring to the current aspect, the wavelength filter may be a single pass gas cell, a multi-pass gas cell, or a hollow core fiber. The wavelength filter may employ hydrogen cyanide or acetylene, or gas with similar absorption features at this wavelength. It is necessary for the molecular absorption filter to be spectrally narrow and strongly absorbing. Therefore low pressure (to prevent pressure broadening) and long path length (for strong absorption) are necessary when using a gas such as hydrogen cyanide. The lidar system may additionally comprise a scanner for scanning the optical beam and receiver field of view relative to at least one scan axis. The lidar system may scan relative to two axes.

In accordance with another aspect of the present invention, a lidar system capable of remote identification of a molecular scattering component of backscattered radiation is provided where the transmitter is capable of transmitting an optical beam having an energy level within the eye safety standards of American National Standard for the Safe Use of Lasers, ANSI Z136.1-2000, and having a pulse energy of a least about 200 mJ/pulse. The system also comprises a receiver capable of detecting the backscatter from the transmitted beam and converting the detected backscatter into electrical signals that form an electrical signature. The electrical signature may include information representing the molecular scattered component of backscattered radiation. The system may further comprise a processor capable of determining the molecular scattered component of the detected backscatter to radiation. The lidar system may also be capable of determining an aerosol-scattered component of the backscattered radiation. The lidar system may also be capable of determining a calibrated, absolute aerosol backscatter coefficient based on, at least in part, analysis of the received backscatter. The lidar system may also be capable of determining the optical thickness of atmospheric aerosol particles based on the analysis of the electrical signals generated by the detected backscatter to radiation.

Furthermore, the optical beam transmitted by the lidar system may have primary wavelength between 1.5 and 1.8 microns. The optical beam may have a wavelength equal to absorption line of hydrogen cyanide.

The transmitter of the lidar system may be comprised of a source laser pump for providing a source beam and a Raman wavelength shifter for shifting the wavelength of the source beam to a second wavelength wherein the transmitted beam has an energy level within the eye safety standards of American National Standard for the Safe Use of Lasers, ANSI Z136.1-2000. The source laser pump may be seeded by a source laser seed laser, which may be tunable to allow for the fine adjustment of the wavelength off the source beam. The Raman wavelength shifter may be seeded by a Raman wavelength shifter seed laser which may be tunable to allow for the fine adjustment of the wavelength of the Raman shifted beam. The Raman wavelength shifter seed laser may be a diode injection seed laser. The source beam may be amplified prior to entering the Raman wavelength shifter. The transmitter of the lidar system may transmit an optical beam having a bandwidth of less than about 200 MHz.

Still referring to the current aspect, the receiver of the lidar system may be comprised of collection optics for collecting backscattered radiation, a collimator for collimating the collected backscattered radiation, a beam splitter for splitting the collimated backscattered radiation into a first post-beam-splitter beam and a second post-beam-splitter beam, first directing optics for directing the first post-beam-splitter beam onto a first detector, and second directing optics for directing the second post-beam-splitter beam into a wavelength filter and onto a second detector. The first detector may be operative for converting the first post-beam splitter beam into a first electrical signal representative of the first post-beam splitter beam. The second detector may be operative for converting the second post-beam splitter beam into a second electrical signal representative of the second post-beam splitter beam. The wavelength filter may be a hydrogen cyanide gas cell. The lidar system may additionally comprise a scanner for scanning relative to at least one scan axis.

In accordance with another aspect of the present invention, a transmitter capable of transmitting an optical beam having a primary wavelength between about 1.5 and 1.8 microns and a bandwidth of less than about 200 MHz is provided, for example, for use in atmospheric lidar systems. The transmitter may be comprised of a source laser pump generating a source beam having a first wavelength and a Raman wavelength shifter to shift the source beam to a second wavelength between about 1.5 and 1.8 microns. The source laser pump may be seeded by a source laser seed laser, which is tunable with respect wavelength. The Raman wavelength shifter may be seeded by a Raman wavelength shifter seed laser, which may be tunable with respect to wavelength. The transmitted optical beam may have a pulse energy of at least about 200 mJ/pulse. The transmitted optical beam may have an energy level within the eye safety standards of American National Standard for the Safe Use of Lasers, ANSI Z136.1-2000. The transmitted optical beam may have a wavelength equal to an absorption line of hydrogen cyanide.

In accordance with another aspect of the present invention, a transmitter capable of transmitting an optical beam having an energy level within the eye safety standards of American National Standard for the Safe Use of Lasers, ANSI Z136.1-2000, a pulse energy of at least about 200 mJ/pulse and a bandwidth of less than about 200 MHz is provided, for example, for use in atmospheric lidar systems. The transmitter may be comprised of a source laser pump generating a source beam having a first wavelength and a Raman wavelength shifter to shift the source beam to a second wavelength between about 1.5 and 1.8 microns. The source laser pump may be seeded by a source laser seed laser, which is tunable with respect wavelength. The Raman wavelength shifter may be seeded by a Raman wavelength shifter seed laser, which may be tunable with respect to wavelength.

In accordance with another aspect of the present invention, a receiver capable of filtering out specific narrow bands of backscattered radiation between about 1.5 and 1.8 microns is provided, for example, for use in atmospheric lidar systems. The receiver may be comprised of a collimator for collimating the collected backscattered radiation, a beam splitter for splitting the collimated backscattered radiation into a first post-beam-splitter beam and the second post-beam-splitter beam, first directing optics for directing the first post-beam-splitter beam onto a first detector, and second directing optics for directing the second post-beam-splitter beam into a wavelength filter and onto a second detector. The first detector may be operative for converting the first post-beam splitter beam into a first electrical signal representative of the first post-beam splitter beam. The second detector may be operative for converting the filtered second post-beam splitter beam into a second electrical signal representative of the filtered second post-beam splitter beam. The wavelength filter may be a hydrogen cyanide gas cell. The first detector may be a combined channel detector and the second detector may be a molecular channel detector.

In accordance with a further aspect of the present invention, a methodology is provided for remotely measuring atmospheric molecular scattering. The methodology comprises transmitting an optical beam having a primary wavelength of between about 1.5 and 1.8 microns to induce scattered radiation that has a molecular scattered component and an aerosol scattered component, receiving backscattered radiation of the optical beam, filtering the received backscattered radiation, and analyzing the filtered backscattered radiation to determine molecular scattering. The filtering of the received backscattered radiation may filter out the aerosol-scattered component of the backscattered radiation.

In accordance with a further aspect of the present invention, a methodology is provided for remotely determining calibrated, absolute aerosol particle backscatter coefficients. The methodology comprises transmitting an optical beam having a primary wavelength of between about 1.5 and 1.8 microns to induce scattered radiation that has a molecular scattered component and an aerosol scattered component, detecting backscattered radiation of the optical beam, distinguishing the molecular scattered radiation from the aerosol scattered radiation, and determining calibrated, absolute aerosol particle backscatter coefficients based on the detected backscattered radiation.

Still referring to the current aspect, the transmitted optical beam may have an energy level within the eye safety standards of American National Standard for the Safe Use of Lasers, ANSI Z136.1-2000. The transmitted optical beam may have a bandwidth of less than about 200 MHz. Distinguishing the molecular scattered radiation from the aerosol-scattered radiation may comprise directing a portion of the detected backscattered radiation through a hydrogen cyanide cell.

In accordance with a further aspect of the present invention, a methodology is provided for remotely determining aerosol particle plume structure and calibrated, absolute aerosol particle backscatter coefficients. The methodology comprises scanning an optical beam having a primary wavelength of between about 1.5 and 1.8 microns into an atmosphere to induce scattered radiation that has a molecular scattered component and an aerosol scattered component, detecting backscattered radiation of the optical beam, distinguishing the molecular scattered radiation from the aerosol scattered radiation, and determining aerosol particle plume structure and calibrated, absolute aerosol particle backscatter coefficients based on the detected backscattered radiation.

In accordance with a further aspect of the present invention, a methodology is provided for remotely determining calibrated, absolute aerosol particle backscatter coefficients. The methodology comprises transmitting an optical beam having an energy level within the eye safety standards of American National Standard for the Safe Use of Lasers, ANSI Z136.1-2000, and a pulse energy of at least about 200 mJ/pulse to induce scattered radiation that has a molecular scattered component and an aerosol scattered component, detecting backscattered radiation of the optical beam, distinguishing the molecular scattered radiation from the aerosol scattered radiation, and determining calibrated, absolute aerosol particle backscatter coefficients based on the detected backscattered radiation. The transmitted optical beam may have a bandwidth of less than about 200 MHz. Distinguishing the molecular scattered radiation from the aerosol-scattered radiation may comprise directing a portion of the detected backscattered radiation for a hydrogen cyanide cell.

In accordance with a further aspect of the present invention, a methodology is provided for generating an optical beam having a primary wavelength of between about 1.5 and 1.8 microns and a bandwidth of less than about 200 MHz, for example, for use in atmospheric lidar systems. The methodology comprises seeding a source laser with a source laser seed laser, generating a source optical beam of a first wavelength with the seeded source laser, seeding a wavelength shifter with a wavelength shifter seed laser, and directing the source optical beam into the seeded wavelength shifter to shift the source optical beam from the first wavelength to a second wavelength having a primary wavelength of between about 1.5 and 1.8 microns and a bandwidth of less than about 200 MHz. The second wavelength may be at a wavelength equal to an absorption line of hydrogen cyanide.

In accordance with a further aspect of the present invention, a methodology is provided for processing backscattered radiation in a lidar system. The methodology comprises receiving backscattered radiation of a lidar system and filtering at least a portion of the backscattered radiation through a hydrogen cyanide gas cell or equivalent narrow band absorption element, i.e., a hollow core or multi-pass cell.

In accordance with a further aspect of the present invention, a methodology is provided for calibrating an absolute aerosol particle backscatter coefficient measuring lidar system. The methodology comprises transmitting an optical beam having a primary wavelength corresponding to an absorption line of hydrogen cyanide, receiving backscattered radiation of the optical beam, splitting the backscattered radiation into first and second beam components, filtering the second beam component through a hydrogen cyanide absorption cell, analyzing the filtered second beam and the first beam to determine measured values for molecular backscattered radiation and aerosol backscattered radiation, determining a calibration factor based, at least in part, on the difference between the measured molecular backscattered radiation and a value for molecular backscattered radiation corrected for extinction, and calibrating the absolute aerosol particle backscatter coefficient measuring lidar system by applying said calibration factor to the measured value for the aerosol scattered component.

Further areas of applicability of the present invention that will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

For a more complete understanding of the present invention and further advantages thereof, reference is now made to the following Detailed Description taken in conjunction with the accompanying drawings, wherein.

DETAILED DESCRIPTION OF THE INVENTION

In the following description, an embodiment of the invention is set forth first in a high level depiction to describe the basic principles involved in isolating and calibrating the aerosol scattered component of backscattered radiation detected by a lidar system. An embodiment of the invention is then described in detail in the context of a high pulse energy and Raman shifted Eye-safe Aerosol Lidar (REAL™) system, which transmits narrow bandwidth energy, determines the aerosol component of the backscattered energy received and calculates a calibrated, absolute aerosol backscatter coefficient. Indeed, the invention has a number of benefits and provides useful results in this regard. However, it will be appreciated that various aspects of the present invention are not limited to such lidar applications. Accordingly, the following description should be understood as exemplifying the invention and not by way of limitation.

Elastic backscatter lidars are useful tools for atmospheric researchers and commercial users because they are capable of showing the distribution of a plume of aerosol particles in the atmosphere in both space and time. Although the backscatter return from these systems is typically uncalibrated, the images they provide are extremely valuable for identification of boundary layer depth, elevated aerosol layers, wave activity, and sources of pollution. Unfortunately, currently useful atmospheric aerosol lidars are generally not capable of providing calibrated data with regard to absolute optical properties of aerosol particles. This is generally because current useful systems are only capable of determining relative optical properties of aerosol particles. While this can be adequate for determining the presence of a plume, it does not yield reliable information about the plume itself, such as the optical thickness of the plume. Since these systems are not calibrated, comparisons of data obtained from different locations and/or at different times are of little value. The ability to determine calibrated, absolute aerosol backscatter coefficients and optical thicknesses of aerosol particles would be of great value and enable meaningful comparison of optical thickness data obtained at different locations and/or at different times.

Figure 1A:
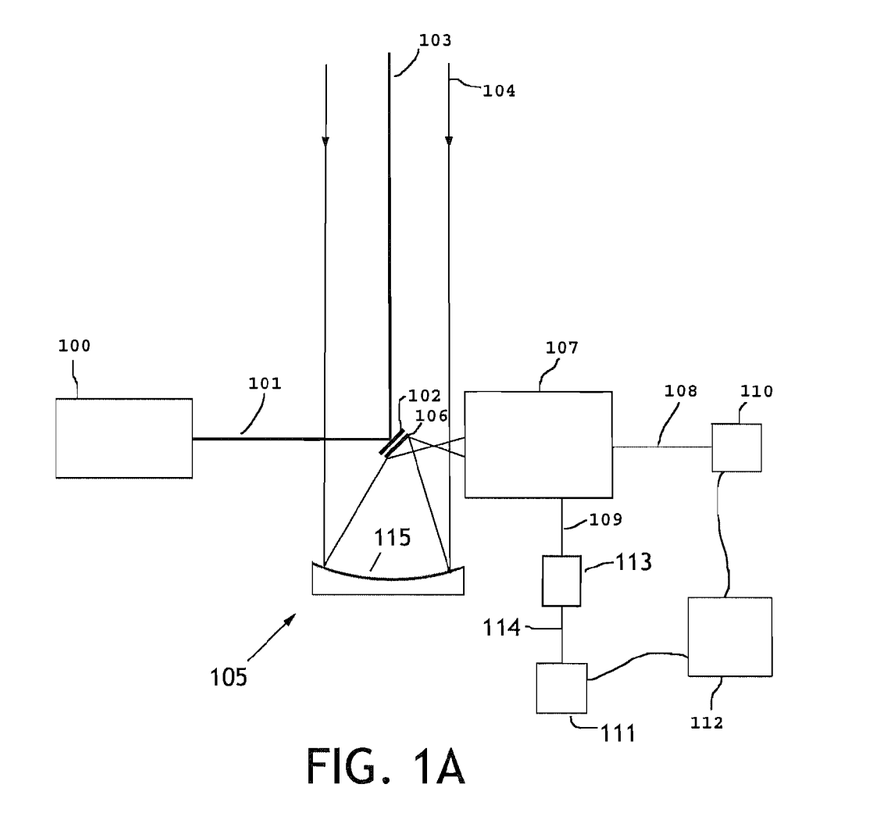
FIG. 1 is a schematic diagram illustrating an atmospheric aerosol particle lidar system transmitting and processing backscattered light in accordance with an embodiment of the present invention.

Current systems of remote identification of calibrated, absolute aerosol backscatter coefficients lack the ability to simultaneously track atmospheric features, such as plume movement, and identify calibrated, absolute aerosol backscatter coefficients. This limitation hinders the usefulness of current systems for use in such critical applications as biological or chemical agent detection and tracking where timely plume and particle data, such as the optical thickness of the plume, are critical. If the types of particles are known along with certain attributes of those particles, particle densities, and hence plume lethality, can be determined. Therefore, development of a high temporal scanning backscatter lidar with the ability to identify calibrated, absolute aerosol backscatter coefficients is a high priority. Also it is preferable that the system be able to operate in an eye-safe matter. The embodiment illustrated in FIG. 2 is such a system and is discussed below. Also discussed below is how the illustrated embodiment of FIG. 2 achieves maximum pulse energy and therefore minimum detection time while operating in an eye-safe manner.

FIG. 1A is a high-level schematic diagram of a system for remotely identifying calibrated, absolute aerosol backscatter coefficients by transmitting spectrally narrow bandwidth energy into the atmosphere and analyzing the scattering characteristics of the backscattered radiation. The system generally includes a beam source 100 of a narrow bandwidth beam of energy 101. The beam source 100 must be capable of generating pulsed light of sufficient power so that the amount of backscatter created by the interaction between the beam of energy 101 and the aerosol particles of interest can be detected.

The spectrally narrow bandwidth beam of energy 101 is generally created by processing a beam from a beam source to achieve the desired intensity, wavelength, and bandwidth. In FIG. 1A, this is represented by the functional block of the beam source 100. The spectrally narrow bandwidth beam of energy 101 may then be directed to a final mirror 102 mounted inside a telescope 105. The final mirror 102 directs the spectrally narrow bandwidth beam of energy 101 into the atmosphere. The spectrally narrow bandwidth beam of energy projected into the atmosphere 103 may be projected along an axis coaxial with the field of view of the telescope 105.

As the beam of energy 103 propagates through the atmosphere, some of the beam energy will interact with atmospheric aerosol particles and molecules and be backscattered along the axis of transmission. This backscattered energy 104 will have spectrum distribution characteristics that are at least partially dependent on the distribution of aerosol particles from which it backscattered. The telescope 105 collects the backscattered energy 104. The system may be utilized in this configuration to obtain vertical images or a scanning system may be disposed in front of the telescope for scanning applications as will be described below. The backscattered energy 104 may be reflected off of a primary mirror 115 and a secondary mirror 106 and directed toward beam processing optics 107. In FIG. 1A, this is represented by the functional block for the beam processing optics 107.

The beam processing optics 107 splits the backscattered energy 104 into two components: a first beam of energy 108 and a second beam of energy 109. The first beam 108 may then be directed to a first beam detector 110. The first beam detector may also be referred to as the combined channel detector. The second beam 109 may be directed into a narrow bandwidth filter 113 resulting in a filtered beam 114, which may be then directed to a second, filtered-beam detector 111. The second beam detector may also be referred to as the molecular channel detector.

The detectors 110 and 111 each provide an electrical output signal that is representative of the optical signal incident on their respective detector surfaces. The electrical output signals, which may be amplified, are fed to a digitizer and computer 112. The digitizer and computer 112 then process the output signals from the detectors 110 and 111 to determine an absolute aerosol backscattering coefficient as described next.

Figure 1B:
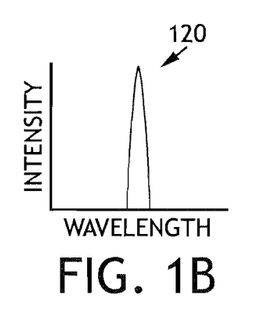

The spectral distribution of the transmitted beam 103 can be represented by the transmission curve 120 in the graph in FIG. 1B. The x-axis of the graph in FIG. 1B represents the wavelength of the transmitted beam 103. The y-axis represents the level of intensity at a given wavelength. The transmission curve 120 represents a very narrow spectral distribution of the transmitted beam.

Figure 1C:
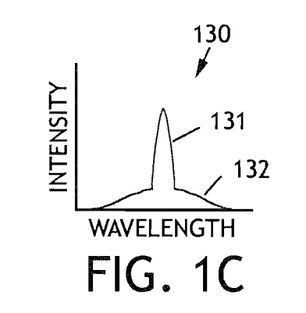

The spectral distribution of the backscattered energy collected by the telescope 105 can be represented by the received backscatter curve 130 in the graph in FIG. 1C. The x-axis of the graph in FIG. 1C represents the wavelength of the received beam 104. The y-axis represents the level of intensity at a given wavelength. FIG. 1C may be a different scale than that in FIG. 1B. The received backscatter curve will generally have two major components: the aerosol backscatter component 131 and the molecular backscatter component 132.

The aerosol backscatter component 131 is a result of the backscattering from the interaction of the transmitted optical beam 103 with atmospheric aerosol particles. The atmospheric aerosol particles are relatively large as compared to the wavelength of the transmitted beam, resulting in Mie scattering, which tends to backscatter energy without significantly shifting the wavelength of the energy. Therefore, the aerosol scattering tends to be at generally the same wavelength as the transmitted beam 103. This is illustrated in FIGS. 1B and 1C where the aerosol backscatter component 131 has a similar shaped distribution as the transmission curve 120.

The molecular backscatter component 132 is a result of the backscattering from the interaction of the transmitted optical beam 103 with atmospheric molecules. The atmospheric molecules are relatively small as compared to the wavelength of the transmitted beam, resulting in Rayleigh scattering, which can shift the wavelength of the backscattered radiation resulting in a wider distribution of wavelength than the transmitted radiation. Therefore, the molecular scattering tends to produce a wider distribution of backscattered energy than that of the transmitted beam 103. This is illustrated in FIG. 1C where the molecular backscatter component 132 has a wider shaped distribution than the transmission curve 120.

Figure 1D:
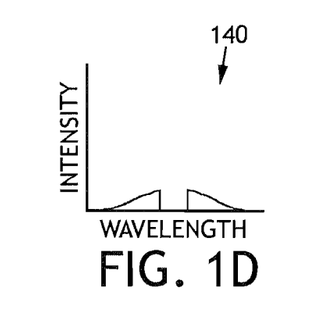

As previously stated, the spectral distribution of the backscattered energy collected by the telescope 105 can be represented by the received backscatter curve 130 in the graph in FIG. 1C. FIG. 1C is also representative of the two beam components 108 and 109 as they exit the beam processing optics 107. As stated previously, beam 108 may be directed to a first beam detector 110. The first beam detector 110 receives backscattered energy represented by the received backscatter curve 130 in the graph in FIG. 1C. Beam 109 may be directed through a narrow bandwidth filter 113. The narrow bandwidth filter 113 may be selected to filter out a narrow bandwidth of backscattered radiation that coincides with the transmission bandwidth shown in FIG. 1B. The effect of the narrow bandwidth filter 113 is that the beam 109 enters the filter with a spectral distribution as shown in FIG. 1C, the energy coinciding with the transmission energy is filtered out, and the filtered beam 114 has a spectral distribution as depicted in FIG. 1D. FIG. 1D may be a different scale than that in FIG. 1B or 1C. FIG. 1D represents the spectral distribution of backscattered energy resulting from molecular scattering with a center portion coinciding with the transmission wavelength filtered out. The filtered beam 114 may be then directed onto a second beam detector 111. Therefore, the second beam detector 111 receives backscattered energy represented by the filtered backscatter curve 140 in the graph in FIG. 1D.

The aerosol backscattering can be determined by subtracting the signal produced by the second beam detector 111 from the signal produced by the first beam detector 110. The remaining signal, after accounting for the molecular scattering that occurs at the transmitted wavelength, is the measured aerosol backscatter.

For a given temperature and pressure at a point in the atmosphere, an absolute molecular scattering coefficient can be calculated. This calculated value can then be compared to the molecular backscatter detected by the second beam detector 111. The difference between the calculated amount and measured amount may be due to factors such as system losses or aerosol particles between the lidar system and the portion of the atmosphere of interest. Other factors may also contribute to the difference. However, these factors will affect the aerosol and molecular scattering measurements equally.

Therefore, the difference between the calculated molecular scattering and measured molecular scattering can be used to determine the absolute aerosol scattering coefficient for the portion of the atmosphere of interest. This can be expressed as:

$$\beta_{back}(r) = \frac{\alpha_{back}(r)}{M_{meas}(r)} A_{meas}(r) \quad (1)$$

Where r is the range from the system to a point in the atmosphere, $\beta_{back}$ is the absolute aerosol backscatter coefficient, $\alpha_{back}$ is the calculated absolute molecular backscatter coefficient, $M_{meas}$ is the measured molecular backscattering, and $A_{meas}$ is the measured aerosol backscatter.

Furthermore, the absolute aerosol backscattering coefficient is related to aerosol concentration by:

$$\beta_{back} = P_d c(t) \pi r^2 Q_{back} \quad (2)$$

where r is the particle radius (m), $Q_{back}$ is the backscatter efficiency of the particle (sr-1), c(t) is the aerosol concentration at time t (kg/m$^3$), and $P_d$ is the aerosol particle density (particles/kg). If $P_d$, r, and $Q_{back}$ are known or can be estimated for a particular particle, aerosol concentration can be determined.

Figure 2:
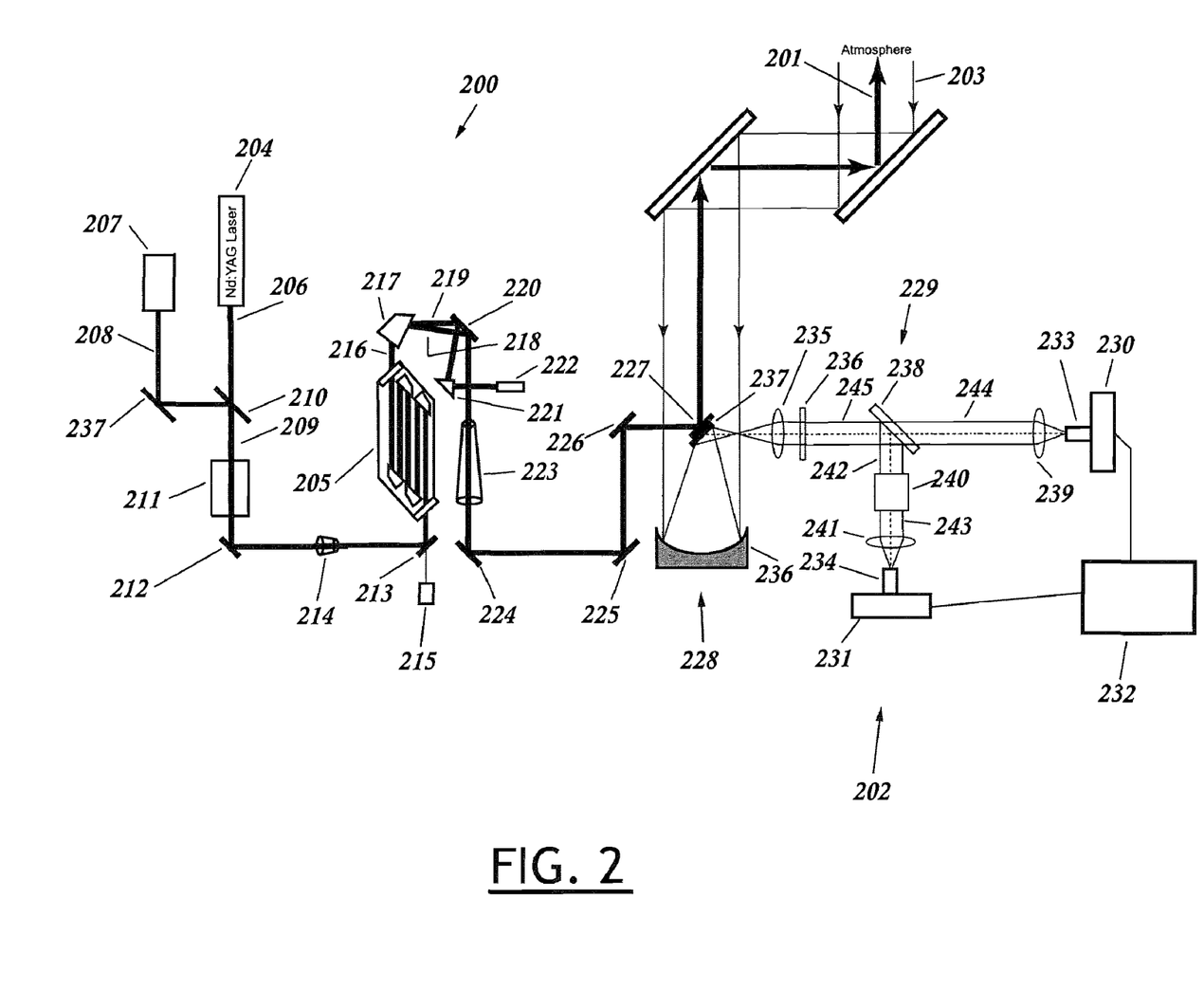
FIG. 2 is a schematic diagram illustrating an alternative embodiment of an atmospheric aerosol particle lidar system in accordance with an embodiment of the present invention.

FIG. 2 is a detailed schematic of an embodiment of the invention set forth in the context of a high-pulse energy and Raman-shifted eye-safe aerosol lidar (REAL™) system constructed in accordance with an embodiment of the present invention. The REAL system generally includes a transmitter 200 for transmitting a low divergence, eye-safe beam 201 into the atmosphere and a receiver 202 for receiving backscattered radiation 203 associated with the transmitted beam 201. The transmitter 200 and receiver 202 are described in turn below.

In the illustrated embodiment, the transmitter 200 includes, among other things, a source pump laser 204 and a Raman cell 205. In this embodiment, the pump laser 204 may be a flash-lamp pulsed, Q-switched, Nd:YAG laser capable of generating 800 mJ/pulse energy at 1064 nm wavelength. Such a pump laser is marketed under the name Continuum Surelite III. Alternatively, the laser may be a more powerful model capable of generating 3 J./pulse at 1064 nm at 10 Hz or 1.2 J at 50 Hz. Such lasers are marketed under the name Continuum Precision TI Series Model 9000 PLUS and Continuum Precision II Series Model 9050. The source pump laser 204 may be injection seeded to produce high spectral purity. The injection seeding is performed by a source laser seed laser 207 which may be a fiber laser. The narrow spectral bandwidth beam 209 from the seeded source pump laser 204 is approximately 9 mm in diameter with a divergence of 0.6 mrad.

The narrow spectral bandwidth beam 209 may be amplified by an amplifier 211. The narrow spectral bandwidth beam 209 is then directed to the Raman cell 205 by way of folding mirrors 212 and 213. As will be discussed below, folding mirror 213 has coating properties so as to allow for transmission of a seed beam through the mirror 213 for coaxial alignment of the seed beam and narrow spectral bandwidth beam 209.

The Raman cell 205 may be a methane Raman cell that operates to convert the narrow spectral bandwidth beam 209 having a wavelength of 1064 nm to a first Stokes wavelength of 1.543 microns, which is within the desired range for eye safety. In order to minimize sooting, while providing a beam of sufficient optical density for enhanced wavelength conversion, a beam reducer 214 may be employed. The illustrated beam reducer 214 is provided via a small Galilean telescope.

In the illustrated embodiment, the narrow spectral bandwidth beam 209 is converted to the eye-safe wavelength via stimulated Raman scattering (SRS) in a pressurized cell filled with pure $CH_4$. SRS is a third-order, nonlinear, inelastic scattering process whereby a sufficiently-high pump field excites molecular vibrations in a medium. The frequency of the scattered light (Stokes output) is shifted by the frequency of these vibrations. Assuming the pump is not depleted, the Stokes intensity as a function of distance is given by the equation:

$$I_S(z) = I_S(0) e^{g_R I_p z} \quad (3)$$

in which $I_S(0)$ is the initial Stokes intensity, $g_R$ is the steady state Raman gain coefficient, $I_p$ is the pump intensity, and z is the interaction length. The gain coefficient is a function of the Raman active medium and its pressure.

The nth Stokes $\lambda_n^S$, and anti-Stokes, $\lambda_n^{AS}$, wavelengths are given by $$\lambda_n^S = \left(\frac{1}{\lambda_p} - \frac{n}{\lambda_R}\right)^{-1} \text{ and } \lambda_n^{AS} = \left(\frac{1}{\lambda_p} - \frac{n}{\lambda_R}\right)^{-1} \quad (4)$$

respectively, where $\lambda_p$ is the pump wavelength, and $\lambda_R$ is the wavelength of the Raman transition. The wavelength of the Raman active symmetric stretch of $CH_4$ is 3.428 microns. Pumping with 1064 nm results in a $1^{st}$ Stokes wavelength of 1543 nm, $2^{nd}$ Stokes wavelength of 2.808 microns and a $1^{st}$ anti-Stokes wavelength of 0.812 microns. As discussed below, the Raman cell may be designed to suppress the buildup of the $2^{nd}$ Stokes and $1^{st}$ anti-Stokes wavelengths.

As seen in Equation 3, the Stokes intensity is a function of pump intensity, pressure of the gas, interaction path length, and the initial Stokes intensity. Typically, the Stokes field is initiated by the spontaneous emission of a photon and therefore the energy and spatial characteristics will fluctuate. To avoid these fluctuations the illustrated cell 205 is seeded with a stable tunable Stokes wavelength Raman seed laser 215. The illustrated Raman seed laser 215 may be, for example, a continuous-wave 20 mW telecom diode laser (Mitsubishi FU-68PDF/520M45B). The illustrated Raman seed laser 215 has a center wavelength of 1543.73 nm and approximately 3 nm tuneability. It is coupled to a single mode, polarization maintaining, fiber which emits a near perfect Gaussian beam. The laser diode driver and associated stable temperature controller (Wavelength Electronics, WLD3343 and WTC3243; respectively) are mounted on a custom circuit board (not shown). The Raman seed laser 215 can be either current or temperature tuned to match the Stokes emission line. To ease alignment, the diode output is amplified via a 1 W fiber amplifier (IPG Photonics Corp., model EAU-1-C) to 100 mW; however, the additional power provides little to no performance enhancement. The output from the laser fiber may be expanded and collimated to match the pump beam diameter, 6 mm, and spatially overlapped by transmitting through the back of the mirror 213, which, in the illustrated implementation, is a gimbal mounted turning mirror. The Raman seed laser can be tuned to match an absorption line of a hydrogen cyanide filter 240 discussed below.

The source pump laser beam may be reduced in diameter from the 9 mm source beam to a 6 mm diameter beam by beam reduce or 214, which may be in the form of a Galilean telescope. In the present embodiment, the Galilean telescope is composed of two 25.4 mm diameter lenses; one plano-convex and one plano-concave, separated by 12 cm. In particular, the plano-convex lens may be a commercially available lens marketed under the name CVI Part No. PLCX-25.4-180.3-UV-1064 and the plano concave lens may be a commercially available lens marketed under the name CVI Part No. PLCC-25.4-128.8-UV-1064. The resulting beam is substantially collimated rather than focused. That is, the rays of the beam are substantially parallel rather than converging relative to any of the optics of Raman cell 205. It is further noted that the pairing of the folding mirrors 212 and 213 allows for improved circularity of the beam entering the Raman cell 205.

Figure 3:
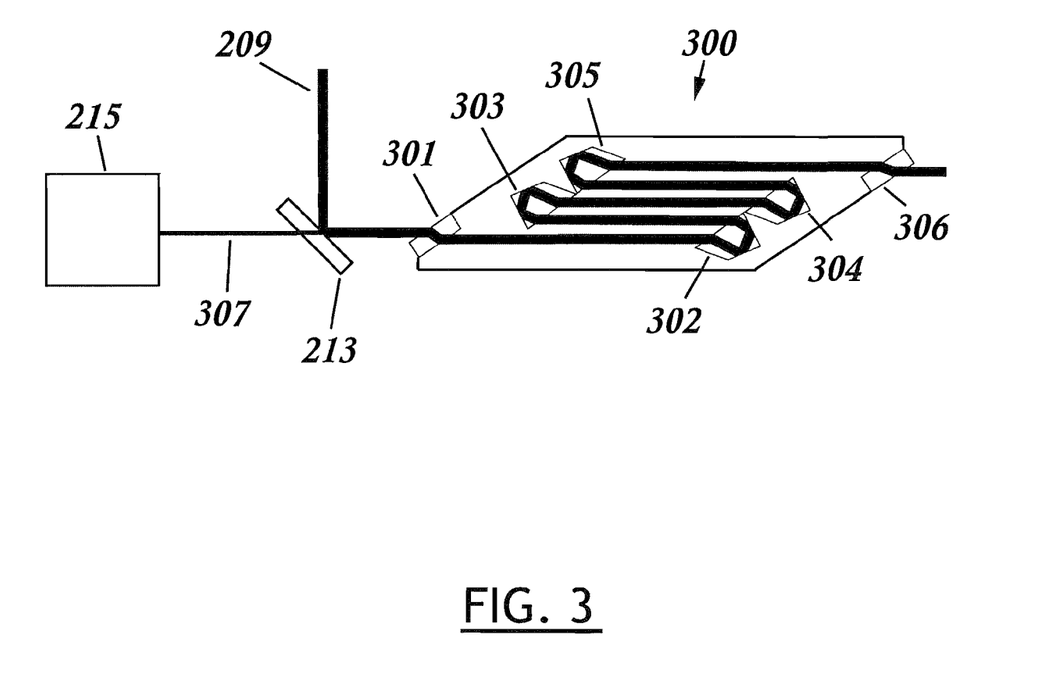
FIG. 3 is a schematic diagram illustrating a Raman wavelength shifter with geometry in accordance with an embodiment of the present invention.

FIG. 3 illustrates an implementation for the Raman cell 300 in accordance with an embodiment of the present invention. The illustrated cell includes an entrance window 301 for allowing transmission of the narrow spectral bandwidth beam 209 together with the seed beam 307 from the Raman seed laser 215 into the interior space of the cell 300, internal reflectance elements 302, 303, 304 and 305, and an exit window 306 for allowing transmission of the wavelength shifted beam out of the interior space of the cell 300.

The entrance and exit windows 301 and 306 are oriented at the Brewster angle with respect to the incident beam to eliminate the need for vulnerable anti-reflective (AR) coatings. The Brewster angle is the angle at which light, in a particular linear polarization state, will pass through an interface without any reflection. The internal reflectance elements 302-305 provide for internal rather than surface reflection of the beams. For example, the elements 302-305 may be prisms. The elements 302-305 thus redirect the light based on total internal reflections thereby eliminating the need for special high-reflection (HR) coatings. In addition to having a high damage threshold, the total internal reflection has negligible loss. The elements 302-305 are also oriented at Brewster angles relative to the incident beams to eliminate the need for AR coatings on their front entrance and exit surface. Moreover, the use of the internal reflectance elements 302-305 eliminates beam overlap geometry that would be associated with surface reflecting mirrors. That is, by translating the beam within the elements 302-305 and then maintaining the beams in a parallel relationship within the cell 300, a larger volume of gas is illuminated for higher total gain than compared to a Raman cell with flat mirrors as internal reflectance elements. The windows 301 and 306 and internal reflectance elements 302-305 may be made of, for example, infrared grade fused silica so that they can be used at any wavelength from the ultraviolet to the near infrared. By not incorporating the AR and HR coatings, the illustrated cell 300 can be used at various wavelengths and will be more durable than a cell incorporating the coatings. The higher order Stokes and anti-Stokes lines can be suppressed, e.g., by controlling cell gas pressure and by injection seeding.

Referring again to FIG. 2, the beam 216 exiting the Raman cell 205 generally includes two wavelength components. Specifically, not all of the optical energy is converted from the source laser pump wavelength to the Raman shifted, eye-safe wavelength. It is often desired to transmit only the eye-safe wavelength into the atmosphere. Accordingly, it may be desired to remove the source laser pump wavelength component. In the illustrated embodiment, a wavelength dispersive element 217, such as a Pellin Broca prism, receives the beam 216 and spatially separates the beam 216 into an eye-safe beam 218 and a source wavelength beam 219. The path of the source wavelength beam 219 is folded by mirror 220 and prism 221 to a beam dump component 222. For example, the beam dump component 222 may be a black box or other light absorber.

The eye-safe beam 218 may be further processed for transmission into the atmosphere. Specifically, in the illustrated embodiment, the eye-safe beam 218 is processed by a beam expander 223 to impart desired beam characteristics. In this regard, it is desirable to expand the eye-safe beam 218 to provide the desired optical density as well as to improve the beam divergence.

The divergence of a laser beam is given by:

$$\Theta = M^2 \frac{2\lambda}{\pi \omega_o} \quad (5)$$

where $\omega_o$ is the beam waist radius, $\lambda$ is the wavelength, and $M^2$ is defined as the ratio of the beam's divergence to that of a diffraction limited beam of the same waist diameter. Note from Equation 5 that the beam divergence can be reduced by improving the beam quality and/or increasing the beam diameter (beam expansion). The illustrated REAL system capitalizes on this Gaussian beam propagation concept in the transmitter design to reduce the divergence of the transmit beam to fit within the receiver's field of view. First, as noted above, the Raman cell is injection seeded to improve beam quality, and second, the beam is expanded prior to transmitting into the atmosphere.

In the illustrated transmitter 200, the eye-safe beam 218 is expanded by expander 223, for example, in the form of a Galilean telescope. Specifically, the illustrated expander 223 is a custom lens system including two air-spaced doublets each antireflection coated for the eye-safe wavelength of 1.543 microns (although the coating could optionally be for dual wavelength operation as well). The first 25.4 mm diameter doublet is a negative lens with a focal length of 138 mm. The second 101.6 mm diameter doublet is a positive lens with a focal length of 574 mm. The doublets are separated by 38 cm and expand the beam 4.3 times. The expanded Stokes beam (about 50 mm diameter) has a half angle divergence of 0.20×0.24 mrad. The resulting expanded, low divergence eye-safe beam is transmitted via a folded path into the atmosphere. Specifically, the path of the beam is folded by folding mirrors 224-227, each of which is coated for high reflection at the desired wavelength or wavelengths.

In the illustrated embodiment, the transmitted beam 201 is transmitted on a path that is coaxial with the backscattered radiation 203. It has been determined via ray tracing that such a coaxial transmit/receive configuration desirably achieves full overlap at 500 meters range with small detectors. Such a coaxial configuration is achieved in the illustrated embodiment by transmitting the beam 201 off the back of the telescope secondary. The expanded beam size is therefore preferably limited to the secondary diameter. In this regard, the mirrors 224-227 of the illustrated embodiment are gold-coated 101.6 mm diameter mirrors at 45 degree angles of incidence. Alternatively, dielectric coatings may be used. The edges of the Stokes beam are clipped slightly in this regard. For a 99% transmission of a true Gaussian beam profile, the mirrors 224-227 would need to be 5 mm larger. The final mirror 227, mounted on the back of the telescope secondary, uses electronically controlled motors, marketed under the name New Focus Picomotors to precisely steer the transmit beam to an angle that is within the receiver field of view. Feedback servo-control based on detector readings may be utilized to optimize steering in this regard.

The illustrated receiver 202 generally includes a telescope 228, receiving optics 229, a beam splitter 238, a first beam detector 233 for detecting the component of the backscattered radiation 203 that is not wavelength filtered, a second beam detector 234 for detecting the component of the backscattered radiation 203 that is wavelength filtered, a first beam signal amplifier 230, a second beam signal amplifier 231, and a digitizer and computer unit 232. Each of these components is described in turn below.

The telescope 228 includes a primary mirror 236 and a secondary mirror 237. The illustrated telescope 228 is a Newtonian telescope with gold-coated mirror surfaces to provide approximately 90% transmission at 1.5 microns. Another option for the telescope 228 is a 40.6 cm diameter f/10 Schmidt-Cassegrain telescope (Meade LX 200 EMC). The noted Schmidt-Cassegrain telescope with gold-coated surfaces provides a transmission of about 72%. Dielectric coatings may alternatively be used in this regard.

The illustrated telescope 228 is mounted in a fixed vertical position. The system may be utilized in this configuration to obtain vertical images or a scanning system may be disposed in front of the telescope for scanning applications as will be described below. In the illustrated system, the backscattered radiation 203 is collected by the telescope 228 and directed to the receiving optics 229.

The received backscattered radiation enters the receiving optics 229 from the telescope 228. The received backscatter may be collimated by collimating lens 235 which may be, for example, a 25.4 mm diameter doublet lens. The collimated beam may be passed through an interference filter 236. The interference filter 236 provides wavelength-dependent filtering to reject noise that could otherwise compete for the dynamic range of the receiver 202. The illustrated filter 236 may be a narrow bandpass interference filter (Omega Optical, Inc. 25.4 mm diameter, 1543.3 nm center wavelength, 5 nm FWHM, with at least 80% transmission).

The illustrated receiving optics 229 further includes a beam splitter 238 to split the collimated and filtered beam 245 into two substantially equal components. A first beam component 244, which passes straight through the beam splitter 238 and a second beam component 242 which may be directed perpendicularly from the first beam component.

Along the beam path of the first beam component 244, the illustrated receiving optics 229 further includes a focusing lens 239 for focusing the first beam component onto the active surface of the first beam detector 233. The first beam detector 233 includes a high gain medium for detection of 1.5 micron wavelength backscattered radiation. A preferred detector for this application is an InGaAs detector. In the illustrated embodiment, the detector is a 200 micron diameter InGaAs/InP avalanche photodiode (Perkins Elmer/EG & G Model No. C30662) with 75% quantum efficiency, a maximum useable gain of approximately 20 and a bandwidth of 200 MHz. More preferably, a detector amplifier unit may be utilized (Perkins Elmer/EG&G Model No. C30659-1550-R2A).

This detector drives the design of the focusing lens 239. The illustrated lens 239 is a three-element design, a doublet with companion meniscus lens, with an 18 mm focal length and 12.4 mm diameter. The lens is designed to collect all light within a 0.15 mrad FOV onto the detector for the range 500 m to 15 km. In practice, the useful range of the instrument is slightly adjustable, analogous to the depth of field of a camera. For example, by moving the position of the detector with respect to the effective focal point of the receiver, the full overlap region can be shifted in either direction. The detector 233, in a shielded enclosure, is mounted on a high precision 3-axis translation stage (Newport ULTRA Line 561D xyz), not shown, for adjustment.

An arrangement similar to the focusing lens 239 and detector 233 along the beam path of the first beam component 244 is located along the beam path of the second beam component 242. However, a wavelength filter 240 may be placed between the beam splitter 238 and a second beam component focusing lens 241. The wavelength filter 240, may be selected to precisely match the wavelength of the transmitted beam 201 and as stated above, the transmitted beam 201 may be fine tuned to match an absorption line of the wavelength filter 240. The illustrated wavelength filter is a hydrogen cyanide absorption filter. Such a filter is marketed under the name C-Band Calibrator Hydrogen Cyanide Gas Cell $H^{13}C^{14}N$ by Wavelength References.

As with the equipment along the beam path of the first beam component 244, there is located along the beam path of the second beam component 242 a focusing lens 241 similar to focusing lens 239 and a second beam detector 234 similar to the first beam detector 233. In the illustrated embodiment, the focusing lenses 239, 241, beam detectors 233, 234, and amplifiers 230, 231 along each beam path 244, 242 are of the same configuration and components.

For each detector 233, 234, the half angle FOV can be given as the photodetector radius divided by the focal length of the receiver system. In one implementation, the effective focal length of the receiver (telescope and custom optics) was calculated to be 367 mm at 1.543 microns. Therefore the receiver FOV, with a 200 micron diameter detector, is 0.27 mrad (half angle). This receiver FOV is slightly larger than the divergence of the transmitted beam 201, which, in the present illustrated embodiment, is about 0.20×0.24 mrad.

The first beam detector 233 provides an electrical output signal that is representative of the optical signal intensity incident on the first beam detector surface. This output signal is then amplified by first beam amplifier 230. In the illustrated embodiment, the amplifier 230 is an operational amplifier (Analog Devices Model ADA29) that has a bandwidth of 55 MHz at a gain of 20. The op amp, photodiode, and power supply are mounted on a custom circuit board in an RF shielded case. In order to amplify return signals that are near the noise level of the detector 233 the noted amplifier 230 is operated with a gain of approximately 850. Unfortunately, this reduces the bandwidth to approximately 1 MHz (350 ns rise time). Operated in this manner, the bandwidth of the amplifier becomes the limiting factor with regard to range resolution. Range resolution can be enhanced in this regard by providing a second stage amplifier.

Similarly, the second beam detector 234 provides an electrical output signal that is representative of the optical signal intensity incident on the second beam detector surface. This output signal is then amplified by second beam amplifier 231. In the illustrated embodiment, the amplifier 231 is also an operational amplifier (Analog Devices Model ADA29) that has a bandwidth of 55 MHz at a gain of 20. As with the first channel, range resolution can be enhanced by providing a second stage amplifier.

The noted two-stage amplifiers allow for realization of potential range resolution on the order of 3 m or better. The lidar system of an embodiment of the present invention may also yield a signal-to-noise ratio of greater than 10 (taking into account the detector noise, background noise from sky radiance and background noise from molecular scattering) at a distance of 15 km for a single laser pulse (or integration time of less than 0.1 seconds) when pointing at an elevation of less than 5° through low altitude haze.

The analog outputs of the amplifiers 230, 231 may be converted to digital signals by at least one analog-to-digital card (GAGE Model 14100) in the digitizer and computer 232, which may be, for example, a personal computer. Each digitizer card may be capable of 14 bit quantization. Each may also be capable of recording one channel at 100 megasamples per second (MSPS) or two channels at 50 MSPS. Programs may be provided in Labview to display the total backscatter data in real-time and write files to the hard disk. Programs may also be provided in the Labview to display the backscatter data for both the incident radiation detected by the first beam detector and by the second beam detector. In addition to acquiring backscatter data for detector, the Labview program is capable of simultaneously monitoring laser energy's location and the temperature and pressure inside the Raman cell via serial connections. The Labview programs can provide total backscatter images, molecular backscatter images, aerosol backscatter images, and absolute aerosol backscatter coefficient images. In addition, such programs can provide for integration of images over a scanning range of interest to provide integrated volume imaging containing total backscatter, molecular backscatter, aerosol backscatter, and absolute aerosol backscatter coefficient components.

Figure 5:
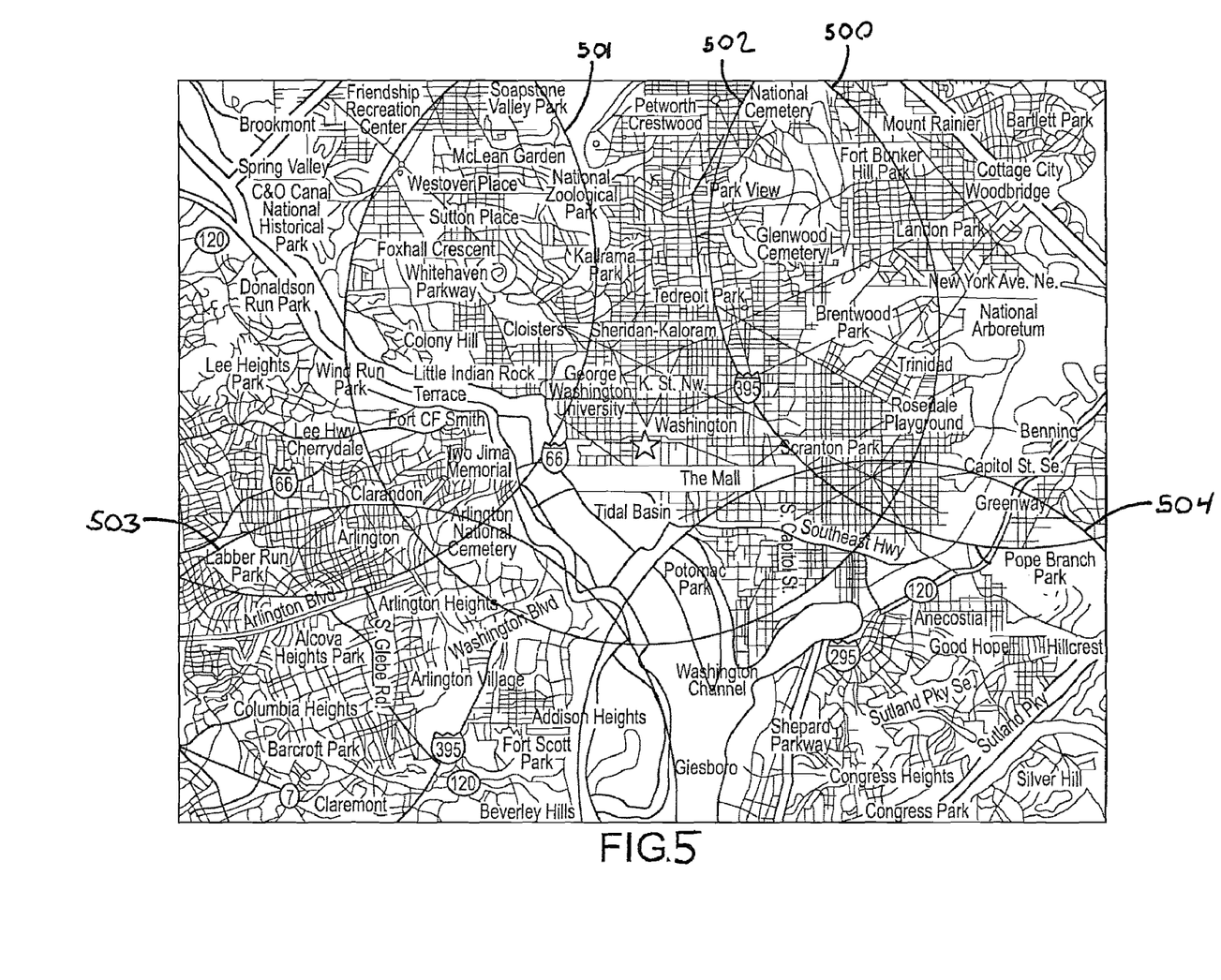
FIG. 5 is a schematic diagram illustrating a network of scanning lidar systems in accordance with an embodiment of the present invention.

As discussed above, it may be desired to scan the transmitted beam across an angular range relative to one or more scan axes. Such scanning capability may be desirable, for example, in connection with operating a network of lidars to identify and monitor aerosols in the atmosphere over a metropolitan area. Such identification and monitoring may be conducted, for example, to determine and monitor sources of pollution or to identify the source of and track harmful agents in the atmosphere. Such a network is schematically illustrated in FIG. 5. Specifically, FIG. 5 illustrates a number of overlapping coverage areas 500-504, schematically illustrated as circles. It will be appreciated that the effective range of each lidar system will vary depending on a number of factors and there is not, in reality, a well-defined edge to any coverage area. However, the various components of the lidar system may be tuned to a desired coverage range. As shown in FIG. 5, the coverage areas may be overlapped to ensure that there are no gaps in coverage or to provide coverage via multiple lidar systems for areas of particular interest. Where adjacent lidar coverage areas overlap, the scanning phase of such neighboring lidar systems may be controlled to provide more frequent coverage in the area of overlap. The network of FIG. 5 corresponds to individual lidar systems that scan a full circular range relative to a vertical axis. Such scanning may be continuous. The lidar systems may also scan across a desired elevation range. In this regard, the scanning relative to the azimuth and elevation axes may be conducted in a raster pattern. The elevation scanning may extend over a 90-degree range so as to define spherical coverage regions associated with each lidar system.

Figure 6:
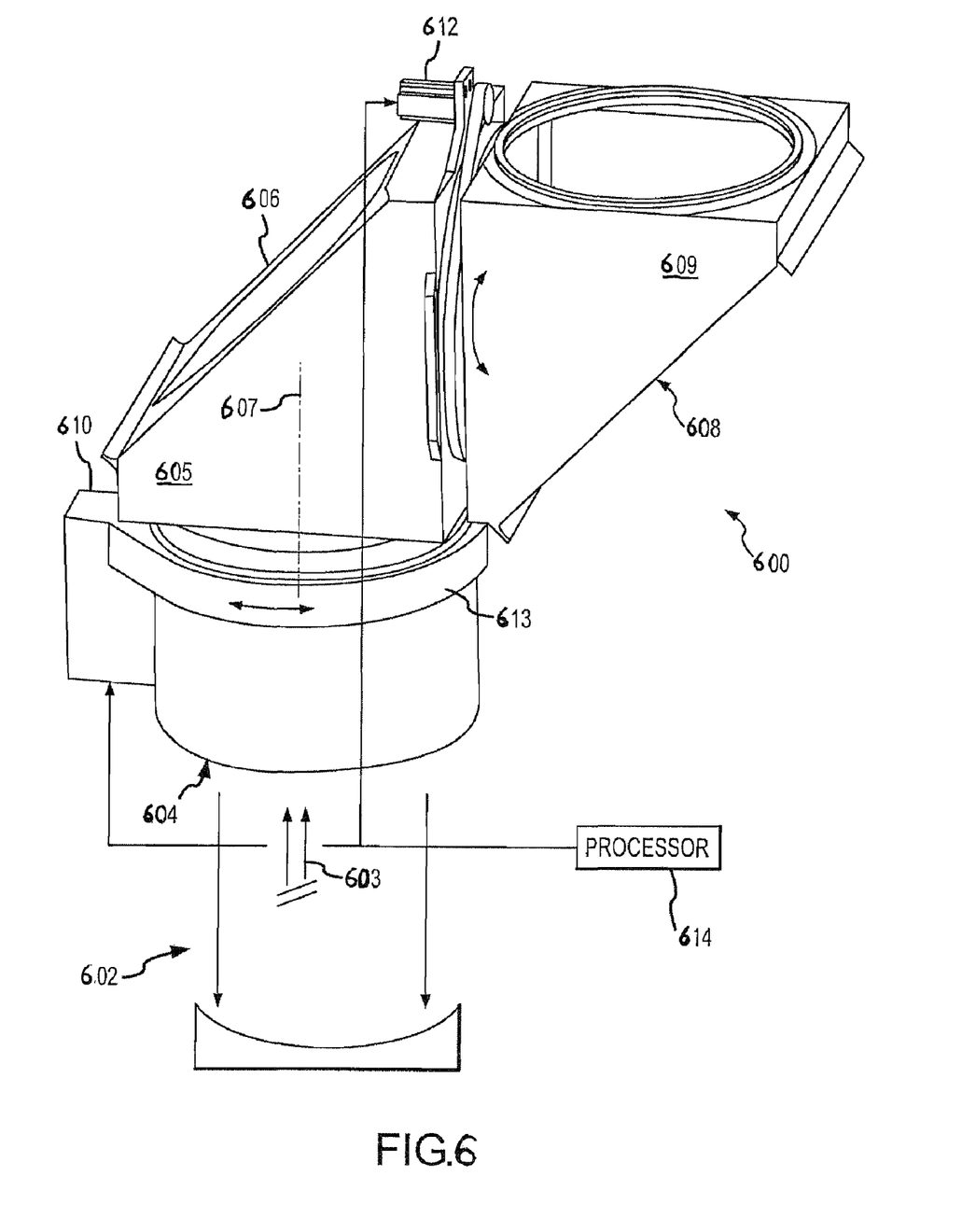
FIG. 6 is a schematic diagram illustrating a scanning system that may be used in connection with the lidar systems of FIG. 1 or FIG. 2.

FIG. 6 illustrates a scanning system 600 for accomplishing such scanning. The scanning system is disposed in front of the telescope 602 of a lidar system. Specifically, a transmitted beam 603 enters the scanning system 600 through an entrance window 604 and is reflected by a first mirror 606 mounted in a first housing section 605 that is rotatable about the telescope optical axis 607. The transmitted beam 603 is redirected by the mirror 606 to a second mirror 608 mounted in a second housing section 609 that is rotatable with respect to the first housing section 605 about an optical axis connecting the mirrors 606 and 608. The combined action of the two mirrors 606 and 608 allows for directing the beam 603 to any desired elevation angle and azimuth angle. The returning backscatter radiation is routed to the telescope 602 by the reverse pathway. It will be appreciated that the mirrors 606 and 608 are movable in a coordinated fashion to direct the transmitted beam and backscatter radiation in this regard. Specifically, a pair of movable mirrors 606 and 608 is used in this regard for enhanced beam circularity and optical efficiency. Moreover, because each mirror 606 or 608 is at a fixed angle relative to the incident beams, the beam footprint on the mirrors does not change and is minimized relative to the full range of scanning angles. The mirrors are driven across the desired range of angular motion by respective azimuth and elevation motors 610 and 612. These motors may be driven by drive signals from the processor 614. The corresponding elevation and azimuth values are recorded by software running on the processor 614 for compiling and recording imaging information.

The illustrated system 600 accommodates continuous 360° azimuth scanning. In this regard, the first housing section 605 may be mounted on a slip ring mounting 613. Because of the coaxial geometry of the lidar system, a single scanning system 600 can be utilized for transmission and reception. Moreover, the illustrated system 600 allows for beam scanning without moving the transmitter and receiver components for improved efficiency and robustness.

As discussed above, the embodiment illustrated in FIG. 2 operates in an eye-safe manner. Operating in an eye-safe manner, as opposed to operating in a non-eye-safe manner, eliminates the requirement that the intended path of a transmitted beam be clear of personnel or objects that could be harmed by a non-eye-safe beam. This enables the use of the system in urban and populated areas and allows for autonomous and continuous operation.

Figure 7:
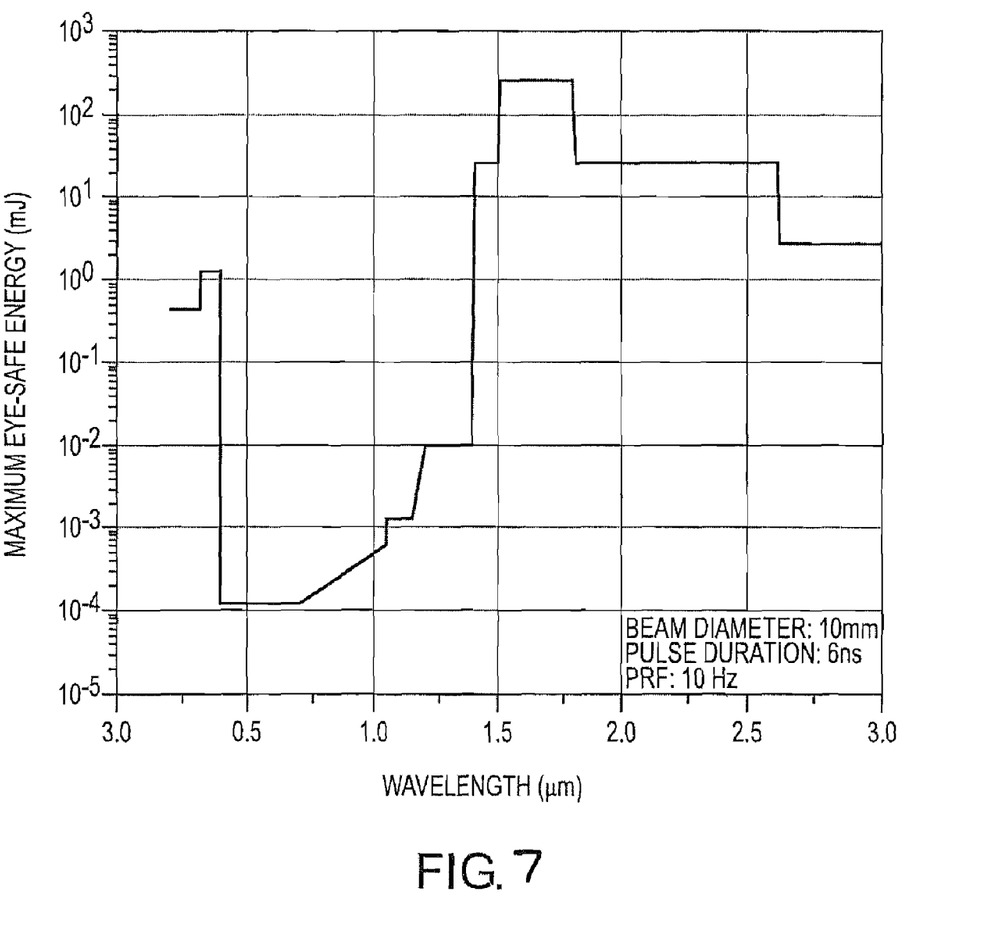
FIG. 7 illustrates the maximum eye-safe energy for a pulse laser according to ANSI standards for particular pulse beam parameters.

There are currently several general approaches for developing an eye-safe lidar. The three broad practical possibilities are: (1) operating at wavelengths less than 0.4 microns, (2) using the micro-pulse technique in the visible part of the spectrum, and (3) operating at wavelengths greater than 1.4 microns. The human eye is particularly vulnerable to wavelengths between 0.4 microns and 1.4 microns because those wavelengths easily pass through the cornea and lens and are focused on the retina. Light at wavelengths less than 0.4 microns and greater than 1.4 microns are safely absorbed in the lens and cornea at the energy densities sufficient for lidar applications. FIG. 7 shows the maximum eye-safe energy (MPE$^2$ times the beam area) for a pulsed laser as a function of beam wavelength permitted under American National Standard for the Safe Use of Lasers, ANSI Z136.1-2000. The chart shows that the region between 1.5 and 1.8 microns has the highest permissible energy. With modest beam expansion it is possible to safely transmit over 1 J per pulse in this region.

The maximum eye-safe energy remains modestly high (similar to 355 nm) for wavelengths longer than 1.4 microns; however, photodetector performance decreases with increasing wavelength. Although Doppler lidars at 2 and 10 microns are successful by using a heterodyne detection method, direct detection lidar in the IR range is best performed at 1.5 microns due to the availability of inexpensive, high quantum efficiency detectors which do not require cooling. Although molecular scattering is lower at infrared wavelengths then at ultraviolet wavelengths, the high pulse energy of this embodiment produces sufficient molecular backscatter to determine an absolute aerosol backscatter coefficient from one pulse of the transmitter. The 1.5 micron wavelength region also features lower sky radiance than a broad range of ultra-violet and visible wavelengths thus improving signal-to-noise ration. When compared to visible region, infrared beams are invisible and therefore eliminate the potential of flash blinding pilots or drawing unwanted attention from the public. Lastly, working in this wavelength allows one to take advantage of recent advancements in the telecommunications sector (e.g., detectors, optical coatings, lasers, etc).

There are a few choices for generating pulsed light in the 1.5 micron wavelength region. The embodiment illustrated in FIG. 2 employs stimulated Raman scattering (SRS) for several reasons including robustness of technique, the quality of the resulting beams including low divergence at the desired power for direct-detection lidar and cost effectiveness.

Figure 4:
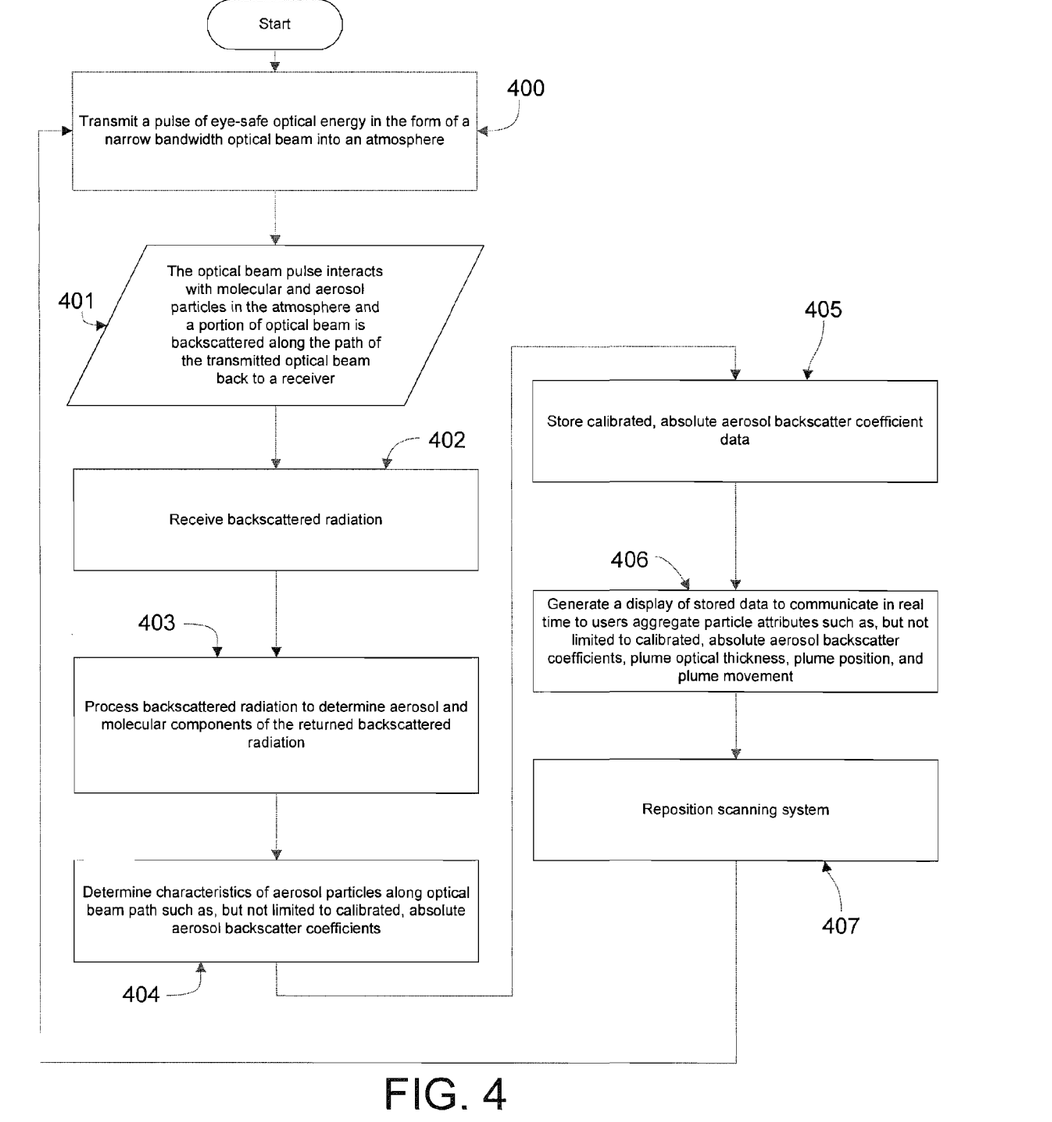
FIG. 4 is a flowchart for a method of remotely identifying aerosol particles in accordance with an embodiment of the present invention.

FIG. 4 illustrates a methodology of remotely determining calibrated absolute aerosol backscatter coefficients in an alternative implementation of the present invention. The illustration is in the form of a flowchart wherein the first step may be to transmit 400 an eye-safe pulse of optical energy in the form of a narrow bandwidth optical beam into an atmosphere. To maximize eye-safe transmission energy the beam pulse may have a primary wavelength between about 1.5-1.8 microns. Next, the transmitted optical beam travels into the atmosphere and interacts 401 with aerosol particles. As a result of this interaction some of the radiation is backscattered along the path of transmission toward a receiver. Some of this backscattered radiation will be from molecular scattering and some will be from aerosol scattering.

The next step may be to receive 402 the backscattered radiation. The following step may be to process 403 the backscattered radiation to determine the molecular and aerosol components of the backscattered radiation. This process may include such steps as collimating the backscattered radiation and splitting the backscattered radiation into at least two beams: a first beam and a second beam. The first beam may be focused on to a first detector to convert the first beam into first electrical signals representative of the total backscattered radiation detected, including both the molecular and aerosol components of the backscattered radiation. The second beam may be directing through a wavelength filter to substantially remove the aerosol backscattered radiation component from the beam, leaving only a molecular component of the backscattered radiation, and focusing the molecular component of the backscattered radiation onto a second detector to convert the molecular component of the backscattered radiation into second electrical signals. An aerosol component of the backscattered radiation can then be determined by subtracting the second electrical signals from the first electrical signals.

The detected molecular and aerosol components of the backscattered radiation may then be used to determine 404 characteristics of the aerosol particles. These characteristics can include, but are not limited to, aerosol particle position, calibrated absolute aerosol backscatter coefficients, and aerosol concentration.

The next step may be to store 405 the characteristics determined in the previous steps 403 and 404. Then the stored information of step 405 can be used to generate 406 a display of the stored data. This display can be in graphical format and can communicate aggregate aerosol particle characteristics such as, but not limited to, aerosol particle plume position, aerosol particle plume movement, calibrated, absolute aerosol backscatter coefficients as a function of position in the atmosphere, and aerosol particle concentration.

The next step may be to reposition 407 an attached scanning system so that the entire process can be repeated looking at a different section of the atmosphere than the previous cycle. It should be noted that the step of repositioning 407 of the scanning system can also be performed at any step after receiving 402 the backscattered radiation but before the next pulse transmission 400.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. A method for calibrating an absolute aerosol particle backscatter coefficient measuring lidar system, comprising the steps of:

scanning an optical beam having a primary wavelength of between about 1.5-1.8 microns through a section of an atmosphere to induce backscattered radiation that has a molecular backscattered radiation component and an aerosol backscattered radiation component, wherein said scanned optical beam has a bandwidth of less than about 200 MHz;

receiving said backscattered radiation of said optical beam;

splitting said received backscattered radiation into first and second beam components;

filtering said second beam component through a wavelength filter, wherein said wavelength filter corresponds to said primary wavelength;

analyzing said filtered second beam component and said first beam component to determine measured values for said molecular backscattered radiation component and measured values for said aerosol backscattered radiation component;

determining a calibration factor based, at least in part, on the difference between the measured molecular backscattered radiation and a value for molecular backscattered radiation corrected for extinction; and calibrating the absolute aerosol particle backscatter coefficient measuring lidar system by applying said calibration factor to said measured value for said aerosol backscattered component.

2. A method for calibrating an absolute aerosol particle backscatter coefficient measuring lidar system, comprising the steps of:

transmitting an optical beam having a primary wavelength corresponding to an absorption line of hydrogen cyanide;

receiving backscattered radiation of said optical beam wherein said received backscattered radiation is comprised of a molecular scattered component and an aerosol scattered component;

splitting said backscattered radiation into first and second beam components;

filtering said second beam component through a hydrogen cyanide cell;

analyzing said filtered second beam component and said first beam component to determine measured values for said molecular scattered component and said aerosol scattered component;

determining a calibration factor based, at least in part, on the difference between the measured molecular backscattered radiation and a value for molecular backscattered radiation corrected for extinction; and calibrating the absolute aerosol particle backscatter coefficient measuring lidar system by applying said calibration factor to said measured value for said aerosol scattered component.

* * * * *

UNITED STATES PATENT AND TRADEMARK OFFICE
CERTIFICATE OF CORRECTION

PATENT NO. : 7,656,526 B1  Page 1 of 1
APPLICATION NO. : 11/459269
DATED : February 2, 2010
INVENTOR(S) : Spuler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 385 days.

Signed and Sealed this

Twenty-eighth Day of December, 2010

David J. Kappos
*Director of the United States Patent and Trademark Office*